(12) United States Patent
Stapper et al.

(10) Patent No.: US 7,732,471 B2
(45) Date of Patent: Jun. 8, 2010

(54) 6-OXAZOL-4-YLMETHOLMETHOXY-ALKO-ALKOXYMETHYL SUBSTITUTED BENZOIC ACID DERIVATIVES FORMING PEROXISOME PROLIFERATOR—ACTIVATED RECEPTOR (PPAR) LIGANDS, PROCESS FOR THEIR PREPARATION AND METHODS OF USE THEREOF

(75) Inventors: Christian Stapper, Frankfurt am Main (DE); Heiner Glombik, Frankfurt am Main (DE); Eugen Falk, Frankfurt am Main (DE); Stefanie Keil, Frankfurt am Main (DE); Hans-Ludwig Schaefer, Frankfurt am Main (DE); Wolfgang Wendler, Frankfurt am Main (DE); Stephanie Hachtel, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/949,833

(22) Filed: Dec. 4, 2007

(65) Prior Publication Data

US 2008/0171776 A1    Jul. 17, 2008

Related U.S. Application Data

(63) Continuation of application No. PCT/EP2006/005570, filed on Jun. 9, 2006.

(30) Foreign Application Priority Data

Jun. 24, 2005   (DE) .................... 10 2005 029 382

(51) Int. Cl.
| A61K 31/421 | (2006.01) |
| C07D 263/32 | (2006.01) |
| A61P 3/08 | (2006.01) |

(52) U.S. Cl. ...................................... 514/374; 548/236
(58) Field of Classification Search ................. 514/374; 548/236
See application file for complete search history.

(56) References Cited

U.S. PATENT DOCUMENTS 6,635,655 B1 * 10/2003 Jayyosi et al. .............. 514/311

FOREIGN PATENT DOCUMENTS

| WO | WO 00/64888 | 11/2000 |
| WO | WO 2004/085377 | 10/2004 |

* cited by examiner

Primary Examiner—Kamal A Saeed
(74) Attorney, Agent, or Firm—Jiang Lin

(57) ABSTRACT

The present invention comprises compounds and compositions for the treatment of metabolic disorders and more particularly, those insulin-related metabolic disorders of the blood such as hyperlipidemia, diabetes, insulin-resistance and the like comprising acetic acid derivatives with cyclohexylmethoxy substituents and their salts. Known as peroxisome proliferator-activated receptor (PPAR) agonists/antagonists, the invention relates to compounds of formula I

I

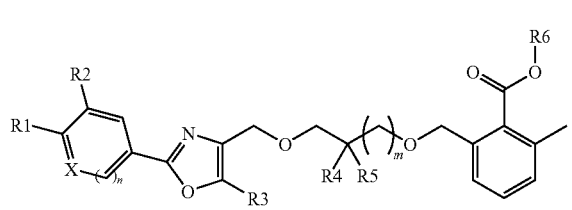

wherein R1-R6 are further defined herein.

21 Claims, No Drawings

6-OXAZOL-4-YLMETHOLMETHOXY-ALKO-ALKOXYMETHYL SUBSTITUTED BENZOIC ACID DERIVATIVES FORMING PEROXISOME PROLIFERATOR—ACTIVATED RECEPTOR (PPAR) LIGANDS, PROCESS FOR THEIR PREPARATION AND METHODS OF USE THEREOF

CROSS REFERENCE TO RELATED APPLICATIONS

This application is a continuation of International application No. PCT/EP2006/005570 filed Jun. 9, 2006, which is incorporated herein by reference in its entirety; which claims the benefit of priority of German Application No. 10 2005029 382.4. filed Jun. 24, 2005.

FIELD OF THE INVENTION

The present invention relates generally to processes for the preparation of compounds and formulations thereof useful in the treatment of metabolic disorders such as hyperlipidemia, diabetes and the consequential cardio-related problems that arise therefrom such as atherosclerosis, serum blood disorders and the like. More specifically, the present invention relates to alkoxymethyl-substituted benzoic acid derivatives, process for their preparation and their use as medicaments and to their physiologically tolerated salts and physiologically functional derivatives which, when formulated as pharmaceutical compositions are therapeutically effective in the treatment of diabetes and allow for the therapeutic modulation of lipid and/or carbohydrate metabolism.

BACKGROUND OF THE INVENTION

The compounds of the present invention are highly effective in the therapeutic modulation of lipid and/or carbohydrate metabolism and are therefore useful in the prevention and/or treatment of diseases such as type-2 diabetes and atherosclerosis, and the many other diverse cardiovascular problems and manifestations arising therefrom.

These compounds have been found to exhibit peroxisome proliferator-activated receptor (PPAR) agonist/antagonist activity, in particular, an excellent PPARalpha modulatory effect as well as a correspondingly excellent PPARgamma modulatory effect.

The peroxisome proliferator-activated receptors (PPAR) are transducer proteins belonging to the steroid/thyroid/retinoid receptor superfamily. The PPAR receptors were originally identified as orphan receptors without known ligands, but were known for their ability to mediate the pleiotropic effects of fatty acid peroxisome proliferators. These receptors function as ligand-regulated transcription factors that control the expression of target genes by binding to their responsive DNA sequences as heterodimers with RXR. The target genes encode enzymes involved in a number of metabolic and cell growth/cell proliferation/cell differentiation inductions. These then provide targets for the development of therapeutic agents for the treatment of metabolic and central nervous system disorders, among others.

PPAR agonists are well known and have been described in the prior art, see U.S. Pat. No. 6,200,995 to De La Brouse-Elwood et. al.; WO 03/043997 to Johnston et. al. and WO 01/00603 and WO 02/092590 to Keil et. al.). comprising an oxadiazolone feature as inhibitors of factor Xa were disclosed in DE 101 12 768 A1 and oxodiazolones have also been described as oral hypoglycemic agents in WO 96/13264. Compounds of similar structure have been described in the art for the treatment of hyperlipidemia and diabetes (WO 2000/064888). Furthermore, WO 2003/010158 describes thiophenecarboxamides and WO2002096863 describes phenylalkyloxy-phenyl-derivatives having no carboxyl group on the phenyl ring.

The invention was based on the object of finding particularly effective compounds allowing a therapeutically usable modulation of lipid and/or carbohydrate metabolism and thus being suitable for the prevention and/or treatment of diseases such as type-2 diabetes, atherosclerosis, and the diverse adverse manifestations thereof.

This has been achieved by selection of the compounds of the formula I described below, which surprisingly show not only a particularly good PPARalpha effect, but also a correspondingly good PPARgamma effect.

SUMMARY OF THE INVENTION

The present invention comprises compounds and compositions for the treatment of metabolic disorders and more particularly, those insulin-related metabolic disorders of the blood such as hyperlipidemia, diabetes, insulin-resistance and the like comprising acetic acid derivatives with cyclohexylmethoxy substituents and their salts. Known as peroxisome proliferator-activated receptor (PPAR) agonists/antagonists, the invention relates to compounds of formula I

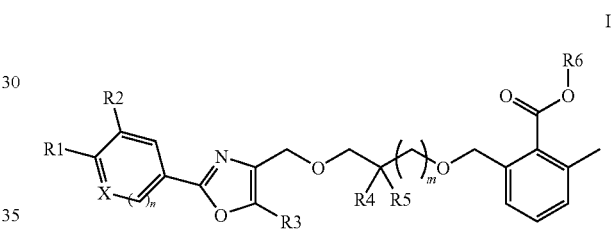

Wherein all the various R-group substituents are defined herein:

DETAILED DESCRIPTION OF THE INVENTION

The present invention comprises compounds and compositions for the treatment of metabolic disorders and more particularly, those insulin-related metabolic disorders of the blood such as hyperlipidemia, diabetes, insulin-resistance and the like comprising acetic acid derivatives with cyclohexylmethoxy substituents and their salts. These peroxisome proliferator-activated receptor (PPAR) agonists/antagonists, which are compounds of formula I as set forth below, surprisingly show not only a particularly good PPARalpha effect, but also a correspondingly good PPARgamma effect and can be synergistically effective when administered in combination with one or more secondary pharmaceutical active compounds useful in the treatment of similar metabolic disorders. These inventive compounds may be defined as follows

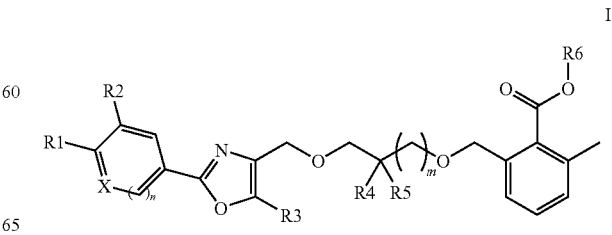

wherein:

R1 is selected from the group consisting of H, (C1-C6)-alkyl, O—(C1-C2)-alkyl, (C1-C6)-alkylmercapto, trifluoromethoxy, trifluoromethylmercapto, F, $CF_3$, phenyl and phenoxy;

R2 is selected from the group consisting of H, O—(C1-C3)-alkyl, (C1-C3)-alkyl, $CF_3$, trifluoromethoxy or when R1 and R2 are fused together with the phenyl ring form a naphthyl;

R3 is selected from the group consisting of H, (C1-C6)-alkyl, phenyl, cyclohexyl;

R4 and R5 are selected from the group consisting of H, and m may be 1, 2, or $CH_3$ with the stipulation that m then must be 1;

R6 is selected from the group consisting of H, (C1-C6)-alkyl;

X is CH, if n=1, or
  S, if n=0;

N is 0 or 1;

M is 1 or 2;

and the pharmaceutically acceptable salts and derivatives thereof.

Preferred compounds of formula I are those in which

R1 or R2 are as defined above with the exception of H.

Particularly preferred compounds of the formula I are those in which

R1 is H;

R2 is selected from the group consisting of O—(C1-C3)-alkyl, (C1-C3)-alkyl, $CF_3$, trifluoromethoxy;

R3 is (C1-C6)-alkyl;

R4, R5 and R6 are H;

X is CH;

n is 1;

m is 1; or more preferably, those PPAR agonists/antagonists are those in which

R1 is selected from the group consisting of (C1-C6)-alkyl, O—(C1-C2)-alkyl, trifluoromethoxy, trifluoromethylmercapto, F, phenyl and phenoxy;

R2 is H;

R3 is (C1-C6)-alkyl, phenyl, cyclohexyl;

R4, R5 and R6 are H;

X is CH;

n is 1;

m is 1 or even more preferably, those PPAR agonists in which

R1 and R2 are both H, $CH_3$, O—$CH_3$ or

R1 and R2 together with the phenyl ring form naphthyl;

R3 is (C1-C6)-alkyl;

R4, R5 and R6 are H;

X is CH;

n is 1;

m is 1.

Further particularly preferred compounds of the formula I are those PPAR agonists/antagonists in which R1 is H, F, $CH_3$;

R2 is H, O—$CH_3$; $CF_3$;

R3 is H, (C1-C6)-alkyl;

R4 and, R5 are $CH_3$;

R6 is H;

X is CH;

n is 1;

m is 1;

or most preferably, those PPAR agonists/antagonists in which

R1 is H, F, $CH_3$, Ph;

R2 is H, O—$CH_3$, $CF_3$;

R3 is (C1-C6)-alkyl;

R4, R5 and R6 are H;

X is CH;

n is 1;

m is 2.

The alkyl groups comprising R1, R2, R3 and R6 may be either straight-chain or branched.

Pharmaceutically acceptable salts are particularly suitable for medical applications because their solubility in water is greater than that of the initial or basic compounds. These salts must have a pharmaceutically acceptable (+) anion or (−) cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

This invention relates further to the use of compounds of the formulae I and their pharmaceutical compositions as PPAR receptor ligands. The PPAR receptor ligands of the invention are suitable as modulators of PPAR receptor activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct., 1993 October, 18(5), 267-77).

The PPAR receptors of the present invention play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. Two variants of PPARgamma exist, PPARgamma$_1$ and gamma$_2$ (Vidal-Puig et al. J. Clin. Invest., 97:2553-2561, 1996). Different PPAR receptors have different tissue distribution and modulate different physiological functions. In addition, however, PPAR receptors are also involved in the regulation of many other physiological processes, including those which are not directly connected with carbohydrate or lipid metabolism. The activity of different PPAR receptors can be modulated by various fatty acids, fatty acid derivatives and synthetic compounds to varying extents. For relevant reviews about functions, physiological effect and pathophysiology, see: Joel Berger et al., Annu. Rev. Med., 2002, 53, 409-435; Timothy Wilson et al., J. Med. Chem., 2000, Vol. 43, No. 4, 527-550; Steven Kliewer et al., Recent Prog Horm Res., 2001, 56, 239-63.

The present invention relates to compounds of the formula I suitable for modulating the activity of PPAR receptors, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med., 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 2001; Sander Kersten, Beatrice Desvergne & Walter Wahli: Roles of PPARs in health and disease, NATURE, VOL 405, 25 MAY 2000; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Compounds of this type are particularly suitable for the treatment and/or prevention of 1.—disorders of fatty acid metabolism and glucose utilization disorders disorders in which insulin resistance is involved 2. Diabetes mellitus, especially type 2 diabetes, including the prevention of the adverse manifestations associated therewith.

Particular aspects in this connection are
hyperglycemia,
improvement in insulin resistance,
improvement in glucose tolerance,
protection of the pancreatic β cells
prevention of macro- and microvascular disorders 3. Dyslipidemias and their sequelae such as, for example, atherosclerosis, coronary heart disease, cerebrovascular disorders etc, especially those (but not restricted thereto) which are characterized by one or more of the following factors:
high plasma triglyceride concentrations, high postprandial plasma triglyceride concentrations,
low HDL cholesterol concentration
low ApoA lipoprotein concentrations
high LDL cholesterol concentrations
small dense LDL cholesterol particles
high ApoB lipoprotein concentrations 4. Various other conditions which may be associated with the metabolic syndrome, such as:
obesity (excess weight), including central obesity
thromboses, hypercoagulable and prothrombotic stages (arterial and venous)
high blood pressure
heart failure such as, for example (but not restricted thereto), following myocardial infarction, hypertensive heart disease or cardiomyopathy 5. Further disorders or conditions in which for example inflammatory reactions or cell differentiation are involved:
atherosclerosis such as, for example (but not restricted thereto), coronary sclerosis including angina pectoris or myocardial infarction, stroke
vascular restenosis or reocclusion
chronic inflammatory bowel diseases such as, for example, Crohn's disease and ulcerative colitis
pancreatitis
other inflammatory states
retinopathy
adipose cell tumors
adipose cell carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc.
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions which are modulated by PPAR
eczemas and neurodermatitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal warts, viral warts such as, for example, molluscum contagiosum, leukoplakia
papular dermatoses such as, for example, lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

The amount of a compound of formula I necessary to achieve the desired biological effect depends on a number of factors, for example the specific compound chosen, the intended use, the mode of administration and the clinical condition of the patient.

The daily dose is generally in the range from 0.001 mg to 100 mg (typically of 0.01 mg and 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, slowly dissolving tablets or tablets, each of which contain a defined amount of the compound of formula I; as powders or granules, as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are mixed together. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agents in a suitable machine. Molded tablets can be produced by molding the compound, which is in powder form and is moistened with an inert liquid diluent, in a suitable machine.

Pharmaceutical compositions which are suitable for peroral (sublingual) administration comprise slow-dissolving tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formulae I are distinguished by favorable effects on metabolic disorders. They beneficially influence lipid and sugar metabolism, in particular they lower the triglyceride level and are suitable for the prevention and treatment of type 11 diabetes and arteriosclerosis and the diverse sequelae thereof.

The compounds of the invention can be administered alone or in combination with one or more additional pharmaceutically active compounds which are also therapeutically effective with respect to metabolic disorders frequently associated therewith. Examples of such pharmaceutically active compounds are:

1. medicaments which lower blood glucose such as antidiabetics,
2. active ingredients for the treatment of dyslipidemias,
3. anti-atherosclerotic medicaments,
4. anti-obesity agents,
5. anti-inflammatory active ingredients
6. anti-tumor agents
7. anti-thrombotic active ingredients 8. active ingredients for the treatment of high blood pressure
9. active ingredients for the treatment of heart failure and
10. active ingredients for the treatment and/or prevention of complications caused by associated with diabetes.

These pharmaceutically active compounds can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Suitable secondary pharmaceutically active compounds include:

Suitable anti-diabetics are disclosed for example in the Rote Liste 2001, chapter 12 or in the USP Dictionary of USAN and International Drug Names, US Pharmacopeia, Rockville 2003. Antidiabetics include all insulins and insulin derivatives such as, for example, Lantus® (see www.lantus-.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S. These patents, as well as all the patent and non-patent references cited below are hereby incorporated by reference herein.

Orally effective hypoglycemic active ingredients include, preferably, sulfonylureas, biguanidines, meglitinides, oxadiazolidinediones, thiazolidinediones, glucosidase inhibitors, glucagon antagonists, oral GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake or food absorption, PPAR and PXR modulators and active ingredients which act on the ATP-dependent potassium channel of the beta cells.

In one embodiment of the invention, the compounds of the formula I are administered in combination with insulin.

In another embodiment of the invention, the compounds of the formula I are combined with substances which influence hepatic glucose production such as, for example, glycogen phosphorylase inhibitors (see: WO 01/94300, WO 02/096864, WO 03/084923, WO 03/084922, WO 03/104188). In yet another embodiment, the compounds of the formula I are administered in combination with a sulfonylurea such as, for example, tolbutamide, glibenclamide, glipizide or glimepiride.

In a third embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In yet another embodiment of the invention, the compounds of the formula I are administered in combination with a biguanide such as, for example, metformin.

In a further embodiment, the compounds of the formula I are administered in combination with a meglitinide such as, for example, repaglinide.

In another embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are in combination with a DPPIV inhibitor as described, for example, in WO 98/19998, WO 99/61431, WO 99/67278, WO 99/67279, WO 01/72290, WO 02/38541, WO 03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]acetyl]pyrrolidine-2-carbonitrile monobenzenesulfonate).

In one embodiment of the invention, the compounds of the formula I are administered in combination with a peroxisome proliferator-activated receptor (PPAR)gamma agonist such as, for example, rosiglitazone, pioglitazone.

In another embodiment, the compounds of the formula I are administered in combination with compounds with an inhibitory effect on SGLT-1 and/or 2, as disclosed directly or indirectly for example in WO 2004/007517, WO 2004/052902 and WO 2004/052903.

In another embodiment, the compounds of the formula I are administered in combination with an α-glucosidase inhibitor such as, for example, miglitol or acarbose.

In another embodiment, the compound of the formula I is administered in combination with inhibitors of acetyl-CoA carboxylase (ACC) such as, for example, those as described in WO199946262, WO200372197, WO2003072197, WO2005044814.

In another embodiment, the compound of the formula I is administered in combination with an inhibitor of phosphoenolpyruvate carboxykinase (PEPCK), such as, for example, those as described in WO2004074288.

In one embodiment, the compound of the formula I is administered in combination with an inhibitor of glycogen synthase kinase-3 beta (GSK-3 beta), as described for example in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In yet another embodiment, the compound of the formula I is administered in combination with an inhibitor of protein kinase C beta (PKC beta), such as, for example, ruboxistaurin.

In another embodiment, the compound of the formula I is administered in combination with inhibitors of "I-kappa-B kinase" (IKK inhibitors) like those described for example in WO2001000610, WO2001030774, WO2004022553, WO2005097129.

In one embodiment, the compound of the formula I is administered in combination with modulators of the glucocorticoid receptor like those described for example in WO2005090336.

In yet another embodiment, the compound of the formula I is administered in combination with inhibitors of acetyl-CoA carboxylase (ACC) such as, for example, those as described in WO199946262, WO200372197, WO2003072197, WO2005044814.

In one embodiment, the compound of the formula I is administered in combination with an inhibitor of phosphoenolpyruvate carboxykinase (PEPCK), such as, for example, those as described in WO2004074288.

In another embodiment, the compound of the formula I is administered in combination with an inhibitor of glycogen synthase kinase-3 beta (GSK-3 beta), as described for example in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of protein kinase C beta (PKC beta), such as, for example, ruboxistaurin.

In one embodiment, the compound of the formula I is administered in combination with an endothelin-A receptor antagonist such as, for example, avosentan (SPP-301).

In one embodiment, the compound of the formula I is administered in combination with inhibitors of "I-kappaB kinase" (IKK inhibitors) like those described for example in WO2001000610, WO2001030774, WO2004022553, WO2005097129.

In one embodiment, the compound of the formula I is administered in combination with modulators of the glucocorticoid receptor like those described for example in WO2005090336.

In one embodiment, the compound of the formula I is administered in combination with an endothelin-A receptor antagonist such as, for example, avosentan (SPP-301).

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid absorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a second peroxisome proliferator-activated receptor agonist/antagonist (PPARalpha) agonist.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compound of the formula I is administered in combination with a PPAR delta agonist such as, for example, GW-501516.

In one embodiment, the compound of the formula I is administered in combination with inhibitors of hormone-sensitive lipase (HSL), as described, for example, in WO 2005073199.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Anti-Obesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

Cannabinoid receptor 1 antagonists (such as, for example, rimonabant, surinabant, azetidine derivatives and/or those as described in, for example, EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897);

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g.1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists).

In one embodiment of the invention, the further active ingredient is leptin.

In one embodiment, the further active ingredient is dexamphatamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with anti-inflammatory agents.

In one embodiment, the compounds of the formula are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow.

The activity of the compounds was tested as follows:

Determination of EC50 Values of PPAR Agonists in the Cellular PPARalpha Assay

The potency of substances which bind to human PPARalpha and activate it in an agonistic manner is analyzed using a stably transfected HEK cell line (HEK=human embryonic kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only little expression of the luciferase reporter gene without addition of a PPARalpha ligand if fatty acid-depleted fetal calf serum (cs-FCS) is used in the assay. PPARalpha ligands bind and activate the PPARalpha fusion protein and thereby bring about expression of the luciferase reporter gene. The luciferase which is formed can be detected by means of chemiluminescence via an appropriate substrate.

Construction of the Cell Line

The PPARalpha reporter cell line was prepared in two steps. Firstly, the luciferase reporter element was constructed and stably transfected into HEK cells. For this purpose, five binding sites of the yeast transcription factor GAL4 (in each case 5'-CGGAGTACTGTCCTCCGAG-3') were cloned in 5'-upstream of a 68 bp-long minimal MMTV promoter (Genbank Accession #V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete *Photinus pyralis* luciferase gene (Genbank Accession #M15077) was cloned in 3'-downstream of the GAL4-MMTV element. After sequencing, the luciferase reporter element consisting of five GAL4 binding sites, MMTV promoter and luciferase gene was subcloned into a plasmid which confers zeozin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeozin-containing medium (0.5 mg/ml) was used to select a suitable stable cell clone which showed very low basal expression of the luciferase gene.

In a second step, the PPARalpha fusion protein (GR-GAL4-humanPPARalpha-LBD) was introduced into the stable cell clone described. For this purpose, initially the cDNA coding for the N-terminal 76 amino acids of the glucocorticoid receptor (Genbank Accession #P04150) was linked to the cDNA section coding for amino acids 1-147 of the yeast transcription factor GAL4 (Genbank Accession #P04386). The cDNA of the ligand-binding domain of the human PPARalpha receptor (amino acids S167-Y468; Genbank Accession #S74349) was cloned in at the 3' end of this GR-GAL4 construct. The fusion construct prepared in this way (GR-GAL4-humanPPARalpha-LBD) was subcloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-humanPPARalpha-LBD) was isolated by selection with zeozin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM medium (#41965-039, Invitrogen) which is mixed with the following additions: 10% cs-FCS (fetal calf serum; #SH-30068.03, Hyclone), 0.5 mg/ml zeozin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (#353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM medium described and counted in a cell counter. After dilution to 500 000 cells/ml, 35 000 cells are seeded in each well of a 96-well microtiter plate with a clear plastic base (#3610, Corning Costar). The plates are incubated in a cell culture incubator at 37° C. and 5% $CO_2$ for 24 h.

Day 2

PPARalpha agonists to be tested are dissolved in DMSO in a concentration of 10 mM. This stock solution is diluted in DMEM medium (#41965-039, Invitrogen) which is mixed with 5% cs-FCS (#SH-30068.03, Hyclone), 2 mM L-glutamine (#25030-024, Invitrogen) and the previously described antibiotics (zeozin, G418, penicillin and streptomycin).

Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96-well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96-well microtiter plate. After incubation at room temperature in the dark for 10 minutes, the microtiter plates are measured in the luminometer (Trilux from Wallac). The measuring time for each well of a microtiter plate is 1 sec.

The raw data from the luminometer are transferred into a Microsoft Excel file. Dose-effect plots and EC50 values of PPAR agonists are calculated using the XL.Fit program as specified by the manufacturer (IDBS).

Determination of EC50 Values of PPAR Agonists in the Cellular PPARgamma Assay

A transient transfection system is employed to determine the cellular PPARgamma activity of PPAR agonists. It is based on the use of a luciferase reporter plasmid (pGL3basic-5xGAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5xGAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3'), together with a 160 bp-long thymidine kinase promoter section (Genbank Accession #AF027128) 5'-upstream into pGL3basic. 3'-downstream of the thymidine kinase promoter is the complete luciferase gene from *Photinus pyralis* (Genbank Accession #M15077), which is already a constituent of the plasmid pGL3basic used. The cloning and sequencing of the reporter plasmid pGL3basic-5xGAL4-TK took place in analogy to the description in Sambrook J. et. al. (Molecular cloning, Cold Spring Harbor Laboratory Press, 1989).

The PPARgamma expression plasmid pcDNA3-GAL4-humanPPARgammaLBD was prepared by first cloning the cDNA coding for amino acids 1-147 of the yeast transcription factor GAL4 (Genbank Accession #P04386) into the plasmid pcDNA3 (from Invitrogen) 3'-downstream of the cytomegalovirus promoter. Subsequently, the cDNA of the ligand-binding domain (LBD) of the human PPARgamma receptor (amino acids I152-Y475; Accession #g1480099) 3'-downstream of the GAL4 DNA binding domain was cloned. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5xGAL4-TK and the PPARgamma expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM medium (#41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

A transfection mixture (solution A) which contains all four plasmids previously described in a DMEM medium, is prepared. The following amounts are used to make up 3 ml of solution A for each 96-well microtiter plate for an assay: 2622 µl of antibiotic- and serum-free DMEM medium (#41965-039, Invitrogen), 100 µl of reference plasmid pRL-CMV (1 ng/µl), 100 µl of luciferase reporter plasmid pGL3basic-5xGAL4-TK (10 ng/µl), 100 µl of PPARgamma expression plasmid pcDNA3-GAL4-humanPPARgammaLBD (100 ng/µl) and 78 µl of plasmid pBluescript SK(+) (500 ng/µl). Then 2 ml of solution B are prepared by mixing 1.9 ml of DMEM medium (#41965-039, Invitrogen) with 100 µl of PolyFect transfection reagent (from Qiagen) for each 96-well microtiter plate. Subsequently, 3 ml of solution A are mixed with 2 ml of solution B to give 5 ml of solution C, which is thoroughly mixed by multiple pipetting and incubated at room temperature for 10 min.

80%-confluent HEK cells from a cell culture bottle with a capacity of 175 $cm^2$ are washed once with 15 ml of PBS (#14190-094, Invitrogen) and treated with 3 ml of trypsin solution (#25300-054, Invitrogen) at 37° C. for 2 min. The cells are then taken up in 15 ml of DMEM medium (#41965-039, Invitrogen) which is mixed with 10% FCS (#16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250 000 cells/ml. 15 ml of this cell suspension are mixed with 5 ml of solution C for one microtiter plate. 200 µl of the suspension are seeded in each well of a 96-well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM medium (#41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from µM to 100 pM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96-well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% $CO_2$ for 48 h.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the *Renilla luciferase* expressed by the reference plasmid pRL-CMV. After incubation at room temperature in the dark for a further 10 minutes, the chemiluminescence mediated by the *Renilla luciferase* is again measured for 1 sec/well in the measuring instrument.

The raw data from the luminometer are transferred into a Microsoft Excel file. The firefly/*Renilla luciferase* activity ratio is determined for each measurement derived from one well of the microtiter plate. The dose-effect plots and EC50 values of PPAR agonists are calculated from the ratios by the XL.Fit program as specified by the manufacturer (IDBS).

The results for the activities of some compounds of the invention of the formula I are indicated in table I below:

TABLE I

| Example No. | EC50 PPARalpha [µM] | EC50 PPARgamma [µM] |
| --- | --- | --- |
| 3 | 0.0042 | 0.15 |
| 8 | 0.011 | 0.040 |
| 11 | 0.0087 | 0.63 |
| 17 | 0.0037 | 0.091 |
| 22 | 0.022 | 0.71 |
| 23 | 0.088 | 1.8 |
| 27 | 0.013 | 0.39 |
| 31 | 0.0014 | 0.017 |
| 32 | 0.0016 | 0.072 |
| 33 | 0.021 | 0.014 |
| * | 0.0010 | >10 |

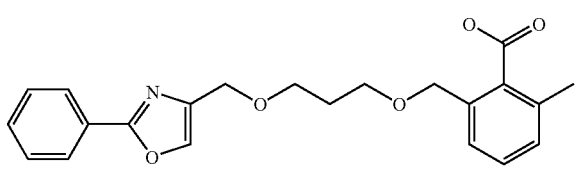

It is evident from table I that the compounds of the invention of the formula I activate the PPARalpha receptor and the PPARgamma receptor and thus for example bring about a lowering of triglycerides in the body in analogy to fibrates in clinical use (see, for example, J.-Ch. Fruchard et al.,: PPARS, Metabolic Disease and therosclerosis, Pharmacological Research, Vol. 44, No. 5, 2001; S. Kersten et al.: Roles of PPARs in health and disease, NATURE, VOL 405, 25 MAY 2000; I. Pineda et al.: Peroxisome proliferator-activated receptors: from transcriptional control to clinical practice, Curr Opin Lipidol 12: 2001, 245-254).

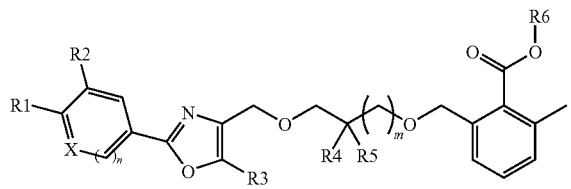

I

TABLE II

Examples 1 to 23 comprise compounds of I with m = 1, R4 = R5 = R6 = H. Me = $CH_3$; Et = $Ch_2CH_3$

| Example | R1 | R2 | R3 | X | n |
|---|---|---|---|---|---|
| 1 | H | Me | Me | CH | 1 |
| 2 | Me | H | Me | CH | 1 |
| 3 | Ph | H | Me | CH | 1 |
| 4 | OCF3 | H | Me | CH | 1 |
| 5 | H | H | Me | S | 0 |
| 6 | SCF3 | H | Me | CH | 1 |
| 7 | F | H | Me | CH | 1 |
| 8 | PhO | H | Me | CH | 1 |
| 9 | H | CF3 | Me | CH | 1 |
| 10 | H | OMe | Me | CH | 1 |
| 11 | OMe | OMe | Me | CH | 1 |
| 12 | H | OCF3 | Me | CH | 1 |
| 13 | tBu | H | Et | CH | 1 |
| 14 | 2-naphthyl | | Et | CH | 1 |
| 15 | Me | Me | Et | CH | 1 |
| 16 | Me | H | Et | CH | 1 |
| 17 | H | OMe | Et | CH | 1 |
| 18 | tBu | H | iPr | CH | 1 |
| 19 | 2-naphthyl | | iPr | CH | 1 |
| 20 | H | CF3 | iPr | CH | 1 |
| 21 | Me | Me | iPr | CH | 1 |

TABLE II-continued

Examples 1 to 23 comprise compounds of I with m = 1, R4 = R5 = R6 = H. Me = $CH_3$; Et = $Ch_2CH_3$

| Example | R1 | R2 | R3 | X | n |
|---|---|---|---|---|---|
| 22 | Me | H | Cy | CH | 1 |
| 23 | Me | H | Ph | CH | 1 |

TABLE III

Examples 24 to 28 with m = n = 1, R4 = R5 = Me, R6 = H, X = CH.

| Example | R1 | R2 | R3 |
|---|---|---|---|
| 24 | F | H | H |
| 25 | Me | H | Me |
| 26 | F | H | Me |
| 27 | H | OMe | Me |
| 28 | H | CF3 | iPr |

TABLE IV

Examples 29 to 33 with m = 2, n = 1, R4 = R5 = R6 = H, X = CH.

| Example | R1 | R2 | R3 |
|---|---|---|---|
| 29 | F | H | Me |
| 30 | Me | H | Me |
| 31 | H | OMe | Me |
| 32 | H | CF3 | iPr |
| 33 | Ph | H | Me |

Process of Preparation

The compounds of the invention of the formula I can be obtained in accordance with the following reaction scheme:

Process A:

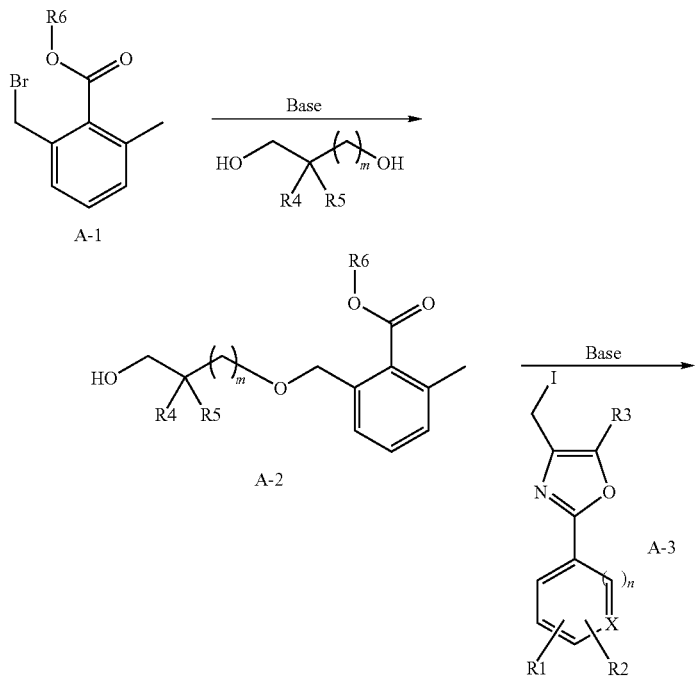

-continued

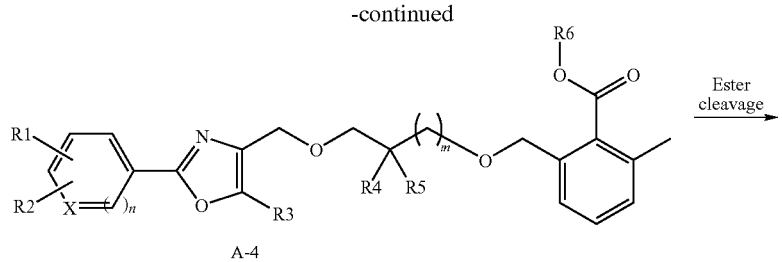

The compound A-1 is prepared by a process described in WO2004076390, where R6 has the meaning described above. This bromide is then reacted with a primary diol (in excess) in the presence of a base in a polar solvent at 20 to 40° C. to give the product A-2, where R4, R5 and m have the meaning described above. The compound A-2 is then reacted in the presence of a base in a polar solvent with an iodide A-3 prepared as described in WO2004076428, WO2004076427, WO02004076426, WO2004075815, WO2004076390, WO2003020269, (all of which are incorporated herein by reference) in which R1, R2, R3, X and n have the same meanings as described above, at 20 to 40° C. to give the compound A-4. Finally, the compound A-4 is subjected to an ester cleavage by stirring it with hydroxide in a water/methanol or water/ethanol mixture at 0 to 40° C. (for R6=primary or secondary alkyl) or in a trifluoroacetic acid/dichloromethane mixture at 0 to 40° C. (for R6=tertiary alkyl). The examples mentioned below can be synthesized by this process.

The abbreviations used stand for:

tBu tert-Butyl

Cy Cyclohexyl

DCM Dichlormethane

DMF N,N-Dimethylformamide

DMSO Dimethyl sulfoxide

EA Ethyl acetate

EI Electron impact ionization (in MS)

equiv. Equivalent

ESI Electron spray ionization (in MS)

Et Ethyl h Hour

HPLC High pressure, high performance liquid chromatography

LCMS Coupled liquid chromatography-mass spectroscopy

Me Methyl

MS Mass spectroscopy

MTBE tert-Butyl methyl ether

NMR Nuclear magnetic resonance spectroscopy

Ph Phenyl iPr Isopropyl nPr n-Propyl

Rf Retention ratio (in TLC)

RT Room temperature sat. Saturated

TFA Trifluoroacetic acid

THF Tetrahydrofuran

TLC Thin-layer chromatography

Other compounds can be prepared in accordance with the process mentioned above.

Example 1

2-Methyl-6-[3-(5-methyl-2-m-tolyloxazol-4-yl-methoxy)propoxymethyl]benzoic acid

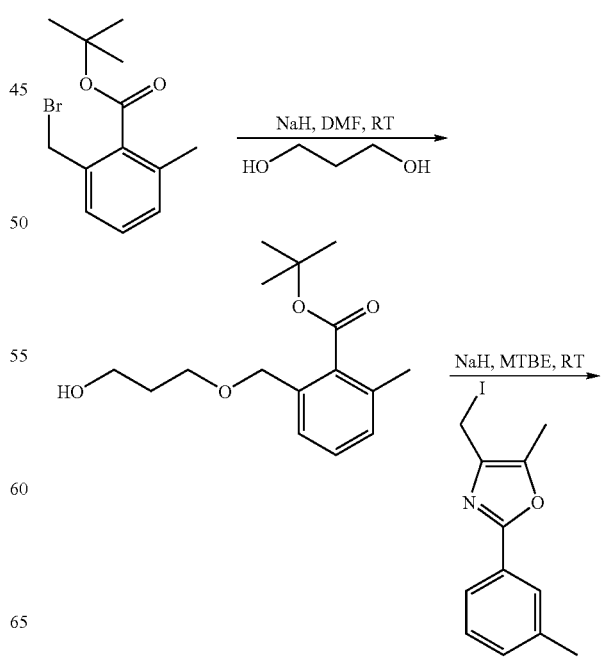

23
-continued

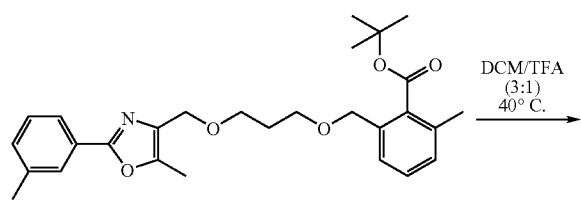

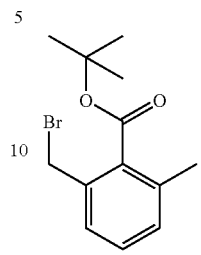 DCM/TFA (3:1) 40° C.

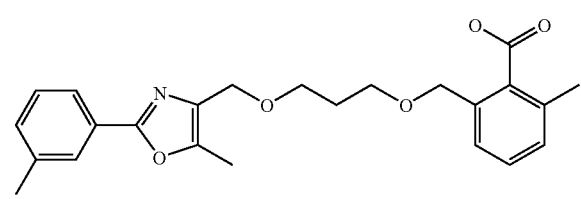

tert-Butyl 2-(3-hydroxypropoxymethyl)-6-methylbenzoate

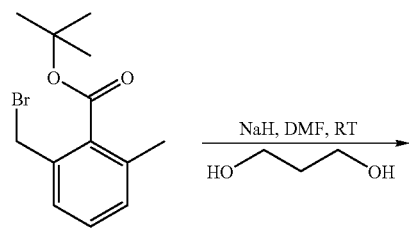 NaH, DMF, RT 25.5 ml of propane diol are slowly added dropwise at RT to a suspension of 3.37 g of sodium hydride (60% by weight in mineral oil) in 400 ml of DMF. After gas evolution ceases, 20 g of tert-butyl 2-bromomethyl-6-methylbenzoate are added, and the solution is stirred at RT for 72 h. Water is added and the solution is extracted twice with MTBE, and the org. phases are combined, washed with water and sat. NaCl solution, dried over MgSO4 and concentrated. The residue is chromatographed on silica gel with a heptane/ethyl acetate gradient, resulting in 16 g of tert-butyl 2-(3-hydroxypropoxymethyl)-6-methylbenzoate as a colorless oil.

1H-NMR (500 MHz, DMSO): δ=7.27-7.32 (m, 1H); 7.16-7.24 (m, 2H); 4.44 (s, 2H); 4.38 (t, J=6 Hz, 1H); 3.39-3.46 (m, 4H); 2.27 (s, 3H); 1.66 (tt, J1=6 Hz, J2=6 Hz, 2H); 1.55 (s, 9H).

24 tert-Butyl 2-(3-hydroxy-2,2-dimethylpropoxymethyl)-6-methylbenzoate

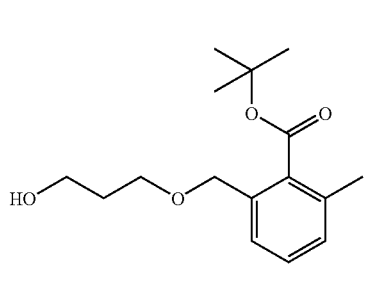 NaH, DMF, RT tert-Butyl 2-(3-hydroxy-2,2-dimethylpropoxymethyl)-6-methylbenzoate is prepared from tert-butyl 2-bromomethyl-6-methylbenzoate and 2,2-dimethylpropane-1,3-diol in analogy to the synthesis of tert-butyl 2-(3-hydroxypropoxymethyl)-6-methylbenzoate.

1H-NMR (500 MHz, DMSO): δ=7.27-7.32 (m, 1H); 7.16-7.24 (m, 2H); 4.44 (s, 2H); 4.39 (t, J=6 Hz, 1H); 3.32-3.40 (m, 4H); 3.16 (d, J=6 Hz, 2H); 3.10 (s, 2H); 2.27 (s, 3H); 1.55 (s, 9H); 0.79 (s, 6H).

tert-Butyl 2-(4-hydroxybutoxymethyl)-6-methylbenzoate

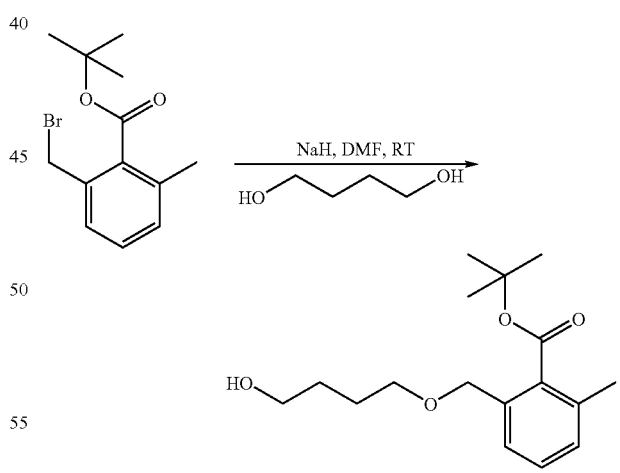

tert-Butyl 2-(4-hydroxybutoxymethyl)-6-methylbenzoate is prepared from tert-butyl 2-bromomethyl-6-methylbenzoate and butane-1,4-diol in analogy to the synthesis of tert-butyl 2-(3-hydroxypropoxymethyl)-6-methylbenzoate.

1H-NMR (500 MHz, DMSO): δ=7.27-7.32 (m, 1H); 7.16-7.24 (m, 2H); 4.44 (s, 2H); 4.37 (t, J=6 Hz, 1H); 3.32-3.40 (m, 4H); 2.27 (s, 3H); 1.55 (s, 9H); 1.50-1.59 (m, 2H); 1.40-1.48 (m, 2H).

2-Methyl-6-[3-(5-methyl-2-m-tolyloxazol-4-yl-methoxy)propoxymethyl]benzoic acid

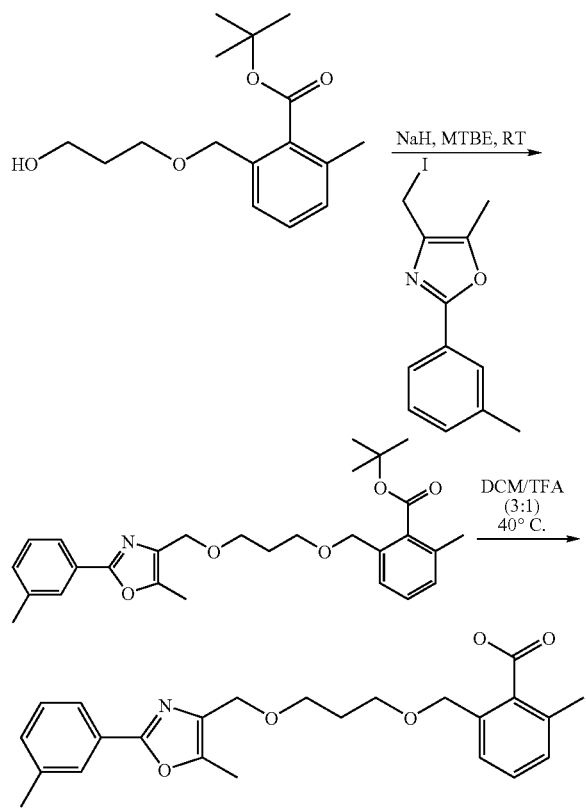

200 mg of tert-butyl 2-(3-hydroxypropoxymethyl)-6-methylbenzoate are dissolved in 1.0 ml of MTBE, and 57 mg of sodium hydride (60% in mineral oil) are added. After gas evolution ceases, 446 mg of 5-methyl-2-m-tolyloxazol-4-yl-methyl iodide are added, and the suspension is stirred at RT overnight. Water is then added, and the solution is poured into a kieselguhr cartridge (VARIAN CHEM ELUT 1010). The product is eluted with MTBE and concentrated. The residue is dissolved without purification in DCM/TFA (3:1) and stirred at 40° C. for 5 h. The solution is concentrated and purified by prep. HPLC, resulting in 202 mg of 2-methyl-6-[3-(5-methyl-2-m-tolyloxazol-4-ylmethoxy)propoxymethyl]benzoic acid.

C24H27NO5 (409.19): LCMS (ESI): 410.48 [MH+].

Example 2

2-Methyl-6-[3-(5-methyl-2-p-tolyloxazol-4-yl-methoxy)propoxymethyl]benzoic acid

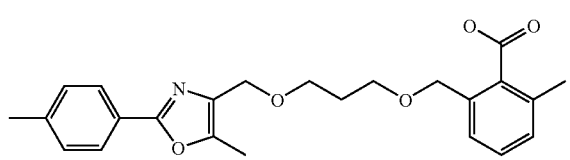

2-Methyl-6-[3-(5-methyl-2-p-tolyloxazol-4-ylmethoxy)propoxymethyl]benzoic acid is obtained from tert-butyl 2-(3-hydroxypropoxymethyl)-6-methylbenzoate and 5-methyl-2-p-tolyloxazol-4-ylmethyl iodide in analogy to example 1.

C24H27NO5 (409.19): LCMS (ESI): 410.23 [MH+].

Example 3

2-Methyl-6-[3-(5-methyl-2-p-biphenyloxazol-4-yl-methoxy)propoxymethyl]benzoic acid

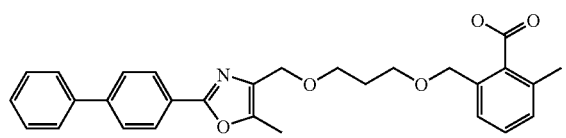

2-Methyl-6-[3-(5-methyl-2-p-biphenyloxazol-4-yl-methoxy)propoxymethyl]benzoic acid is obtained from tert-butyl 2-(3-hydroxypropoxymethyl)-6-methylbenzoate and 5-methyl-2-p-biphenyloxazol-4-ylmethyl iodide in analogy to example 1.

C29H29NO5 (471.20): LCMS (ESI): 472.19 [MH+].

Example 4

2-Methyl-6-{3-[5-methyl-2-(4-trifluoromethoxyphenyl)oxazol-4-ylmethoxy]propoxy-methyl}benzoic acid

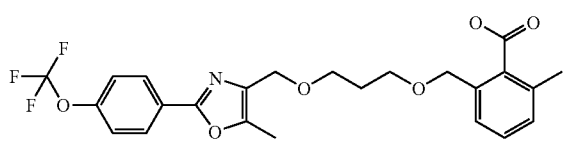

2-Methyl-6-{3-[5-methyl-2-(4-trifluoromethoxyphenyl)oxazol-4-ylmethoxy]propoxy-methyl}benzoic acid is obtained from tert-butyl 2-(3-hydroxypropoxymethyl)-6-methylbenzoate and 5-methyl-2-(4-trifluoromethoxyphenyl)oxazol-4-ylmethyl iodide in analogy to example 1.

C24H24F3NO6 (479.16): LCMS (ESI): 480.12 [MH+].

Example 5

2-Methyl-6-[3-(5-methyl-2-thienyloxazol-4-yl-methoxy)propoxymethyl]benzoic acid

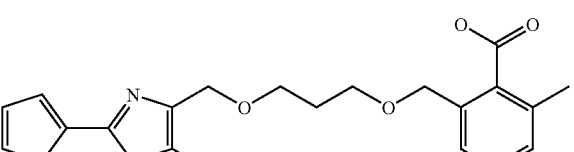

2-Methyl-6-[3-(5-methyl-2-thienyloxazol-4-ylmethoxy)propoxymethyl]benzoic acid is obtained from tert-butyl 2-(3-hydroxypropoxymethyl)-6-methylbenzoate and 5-methyl-2-thienyloxazol-4-ylmethyl iodide in analogy to example 1.

C21H23NO5S (401.13): LCMS (ESI): 402.13 [MH+].

Example 6

2-Methyl-6-{3-[5-methyl-2-(4-trifluoromethylmercaptophenyl)oxazol-4-ylmethoxy]-propoxymethyl}benzoic acid

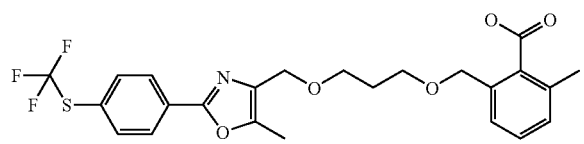

2-Methyl-6-{3-[5-methyl-2-(4-trifluoromethylmercaptophenyl)oxazol-4-ylmethoxy]-propoxymethyl}benzoic acid is obtained from tert-butyl 2-(3-hydroxypropoxymethyl)-6-methylbenzoate and 5-methyl-2-(4-trifluoromethylmercaptophenyl)oxazol-4-ylmethyl iodide in analogy to example 1.

C24H24F3NO5S (495.13): LCMS (ESI): 496.14 [MH+].

Example 7

2-Methyl-6-{3-[5-methyl-2-(4-fluorophenyl)oxazol-4-ylmethoxy]propoxymethyl}-benzoic acid

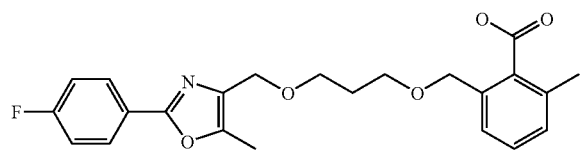

2-Methyl-6-{3-[5-methyl-2-(4-fluorophenyl)oxazol-4-ylmethoxy]propoxymethyl}-benzoic acid is obtained from tert-butyl 2-(3-hydroxypropoxymethyl)-6-methylbenzoate and 5-methyl-2-(4-fluorophenyl)oxazol-4-ylmethyl iodide in analogy to example 1.

C23H24FNO5 (413.16): LCMS (ESI): 414.20 [MH+].

Example 8

2-Methyl-6-{3-[5-methyl-2-(4-phenoxyphenyl)oxazol-4-ylmethoxy]propoxymethyl}-benzoic acid

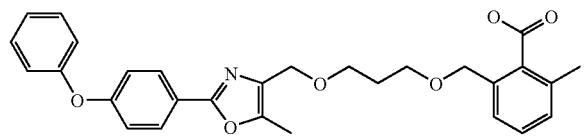

2-Methyl-6-{3-[5-methyl-2-(4-phenoxyphenyl)oxazol-4-ylmethoxy]propoxymethyl}-benzoic acid is obtained from tert-butyl 2-(3-hydroxypropoxymethyl)-6-methylbenzoate and 5-methyl-2-(4-phenoxyphenyl)oxazol-4-ylmethyl iodide in analogy to example 1.

C29H29NO6 (487.20): LCMS (ESI): 488.23 [MH+].

Example 9

2-Methyl-6-{3-[5-methyl-2-(3-trifluoromethylphenyl)oxazol-4-ylmethoxy]propoxy-methyl}benzoic acid

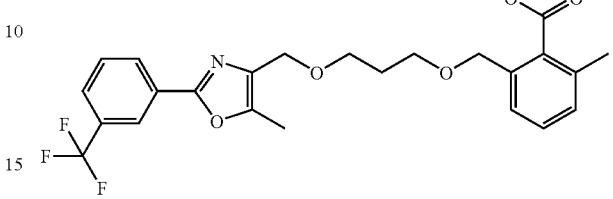

2-Methyl-6-{3-[5-methyl-2-(3-trifluoromethylphenyl)oxazol-4-ylmethoxy]propoxy-methyl}benzoic acid is obtained from tert-butyl 2-(3-hydroxypropoxymethyl)-6-methylbenzoate and 5-methyl-2-(3-trifluoromethylphenyl)oxazol-4-ylmethyl iodide in analogy to example 1.

C24H24F3NO5 (463.16): LCMS (ESI): 464.03 [MH+].

Example 10

2-Methyl-6-{3-[5-methyl-2-(3-methoxyphenyl)oxazol-4-ylmethoxy]propoxymethyl}-benzoic acid

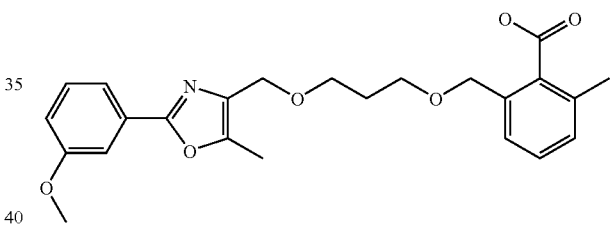

2-Methyl-6-{3-[5-methyl-2-(3-methoxyphenyl)oxazol-4-ylmethoxy]propoxymethyl}-benzoic acid is obtained from tert-butyl 2-(3-hydroxypropoxymethyl)-6-methyl-benzoate and 5-methyl-2-(3-methoxyphenyl)oxazol-4-ylmethyl iodide in analogy to example 1.

C24H27NO6 (425.18): LCMS (ESI): 426.44 [MH+].

Example 11

2-Methyl-6-{3-[5-methyl-2-(3,4-dimethoxyphenyl)oxazol-4-ylmethoxy]propoxymethyl}-benzoic acid

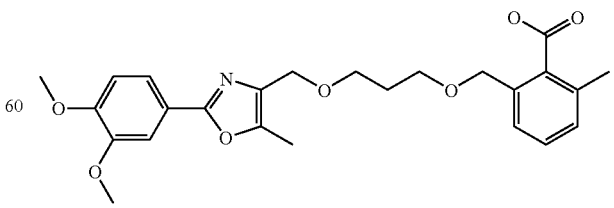

2-Methyl-6-{3-[5-methyl-2-(3,4-dimethoxyphenyl)oxazol-4-ylmethoxy]propoxymethyl}-benzoic acid is obtained from tert-butyl 2-(3-hydroxypropoxymethyl)-6-methyl-benzoate and 5-methyl-2-(3,4-dimethoxyphenyl)oxazol-4-ylmethyl iodide in analogy to example 1.

C25H29NO7 (455.19): LCMS (ESI): 456.18 [MH+].

Example 12

2-Methyl-6-{3-[5-methyl-2-(3-trifluoromethoxyphenyl)oxazol-4-ylmethoxy]propoxy-methyl}benzoic acid

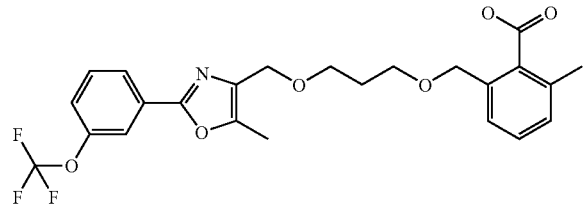

2-Methyl-6-{3-[5-methyl-2-(3-trifluoromethoxyphenyl)oxazol-4-ylmethoxy]propoxy-ethyl}benzoic acid is obtained from tert-butyl 2-(3-hydroxypropoxymethyl)-6-methylbenzoate and 5-methyl-2-(3-trifluoromethoxyphenyl)oxazol-4-ylmethyl iodide in analogy to example 1.

C24H24F3NO6 (479.16): LCMS (ESI): 480.21 [MH+].

Example 13

2-{3-[2-(4-tert-Butylphenyl)-5-ethyloxazol-4-ylmethoxy]propoxymethyl}-6-methyl-benzoic acid

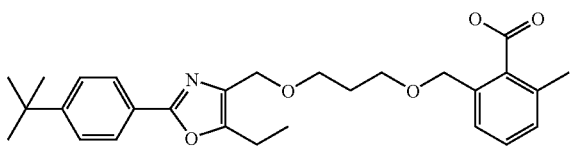

2-{3-[2-(4-tert-Butylphenyl)-5-ethyloxazol-4-ylmethoxy]propoxymethyl}-6-methyl-benzoic acid is obtained from tert-butyl 2-(3-hydroxypropoxymethyl)-6-methyl-benzoate and 2-(4-tert-butylphenyl)-5-ethyloxazol-4-ylmethyl iodide in analogy to example 1.

C28H35NO5 (465.25): LCMS (ESI): 464.24 [MH+].

Example 14

2-{3-[5-Ethyl-2-(2-naphthyl)oxazol-4-ylmethoxy]propoxymethyl}-6-methylbenzoic acid

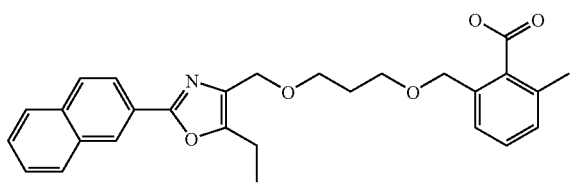

2-{3-[5-Ethyl-2-(2-naphthyl)oxazol-4-ylmethoxy]propoxymethyl}-6-methylbenzoic acid is obtained from tert-butyl 2-(3-hydroxypropoxymethyl)-6-methylbenzoate and 5-ethyl-2-(2-naphthyl)oxazol-4-ylmethyl iodide in analogy to example 1.

C28H29NO5 (459.20): LCMS (ESI): 460.09 [MH+].

Example 15

2-{3-[2-(3,4-Dimethylphenyl)-5-ethyloxazol-4-ylmethoxy]propoxymethyl}-6-methyl-benzoic acid

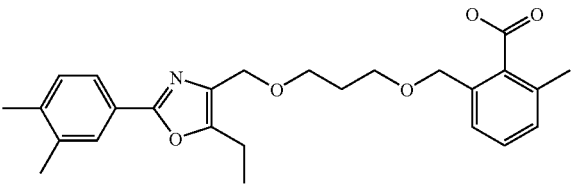

2-{3-[2-(3,4-Dimethylphenyl)-5-ethyloxazol-4-ylmethoxy]propoxymethyl}-6-methyl-benzoic acid is obtained from tert-butyl 2-(3-hydroxypropoxymethyl)-6-methylbenzoate and 5-ethyl-2-(3,4-dimethylphenyl)oxazol-4-ylmethyl iodide in analogy to example 1.

C26H31NO5 (437.22): LCMS (ESI): 438.10 [MH+].

Example 16

2-Methyl-6-[3-(5-ethyl-2-p-tolyloxazol-4-ylmethoxy)propoxymethyl]benzoic acid

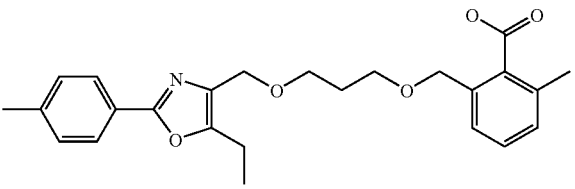

2-Methyl-6-[3-(5-ethyl-2-p-tolyloxazol-4-ylmethoxy)propoxymethyl]benzoic acid is obtained from tert-butyl 2-(3-hydroxypropoxymethyl)-6-methylbenzoate and 5-ethyl-2-p-tolyloxazol-4-ylmethyl iodide in analogy to example 1.

C25H29NO5 (423.20): LCMS (ESI): 424.51 [MH+].

Example 17

2-Ethyl-6-{3-[5-methyl-2-(3-methoxyphenyl)oxazol-4-ylmethoxy]propoxymethyl}-benzoic acid

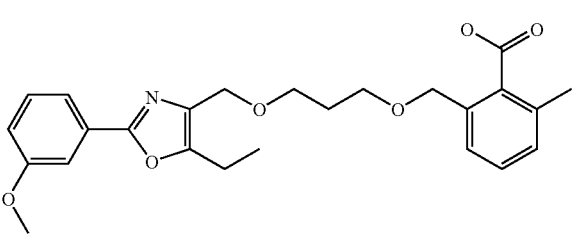

2-Ethyl-6-{3-[5-methyl-2-(3-methoxyphenyl)oxazol-4-ylmethoxy]propoxymethyl}-benzoic acid is obtained from tert-butyl 2-(3-hydroxypropoxymethyl)-6-methylbenzoate and 5-ethyl-2-(3-methoxyphenyl)oxazol-4-ylmethyl iodide in analogy to example 1.

C25H29NO6 (439.20): LCMS (ESI): 440.25 [MH+].

Example 18

2-{3-[2-(4-tert-Butylphenyl)-5-isopropyloxazol-4-ylmethoxy]propoxymethyl}-6-methylbenzoic acid

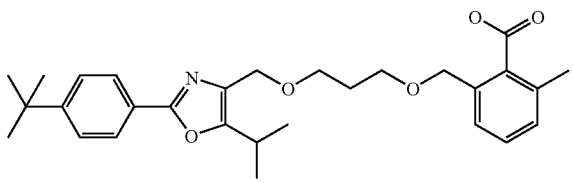

2-{3-[2-(4-tert-Butylphenyl)-5-isopropyloxazol-4-ylmethoxy]propoxymethyl}-6-methyl-benzoic acid is obtained from tert-butyl 2-(3-hydroxypropoxymethyl)-6-methylbenzoate and 2-(4-tert-butylphenyl)-5-isopropyloxazol-4-ylmethyl iodide in analogy to example 1.

C29H37NO5 (479.27): LCMS (ESI): 480.13 [MH+].

Example 19

2-{3-[5-Isopropyl-2-(2-naphthyl)oxazol-4-ylmethoxy]propoxymethyl}-6-methylbenzoic acid

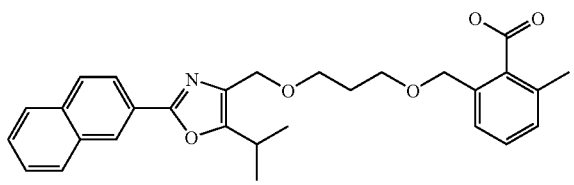

2-{3-[5-Isopropyl-2-(2-naphthyl)oxazol-4-ylmethoxy]propoxymethyl}-6-methylbenzoic acid is obtained from tert-butyl 2-(3-hydroxypropoxymethyl)-6-methylbenzoate and 5-isopropyl-2-(2-naphthyl)oxazol-4-ylmethyl iodide in analogy to example 1.

C29H31NO5 (473.22): LCMS (ESI): 474.09 [MH+].

Example 20

2-{3-[5-Isopropyl-2-(3-trifluoromethylphenyl)oxazol-4-ylmethoxy]propoxymethyl}-6-methylbenzoic acid

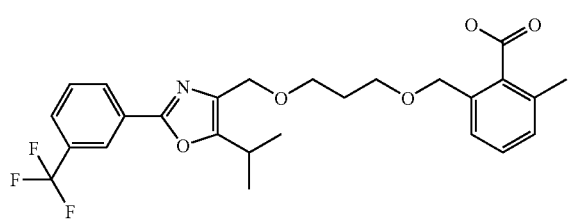

2-{3-[5-Isopropyl-2-(3-trifluoromethylphenyl)oxazol-4-ylmethoxy]propoxymethyl}-6-methylbenzoic acid is obtained from tert-butyl 2-(3-hydroxypropoxymethyl)-6-methylbenzoate and 5-isopropyl-2-(3-trifluoromethylphenyl)oxazol-4-ylmethyl iodide in analogy to example 1.

C26H28F3NO5 (491.19): LCMS (ESI): 492.04 [MH+].

Example 21

2-{3-[5-Isopropyl-2-(3,4-dimethylphenyl)oxazol-4-ylmethoxy]propoxymethyl}-6-methylbenzoic acid

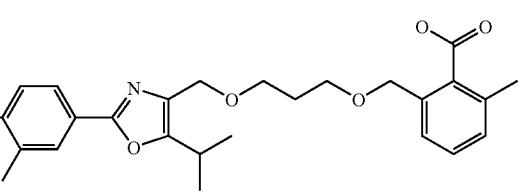

2-{3-[5-Isopropyl-2-(3,4-dimethylphenyl)oxazol-4-ylmethoxy]propoxymethyl}-6-methylbenzoic acid is obtained from tert-butyl 2-(3-hydroxypropoxymethyl)-6-methylbenzoate and 5-isopropyl-2-(3,4-dimethylphenyl)oxazol-4-ylmethyl iodide in analogy to example 1.

C27H33NO5 (451.24): LCMS (ESI): 452.10 [MH+].

Example 22

2-Methyl-6-{3-[5-cyclohexyl-2-p-tolyloxazol-4-ylmethoxy]propoxymethyl}benzoic acid

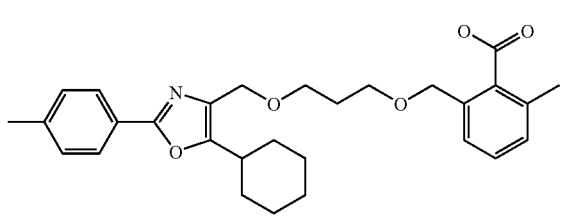

2-Methyl-6-{3-[5-cyclohexyl-2-p-tolyloxazol-4-ylmethoxy]propoxymethyl}benzoic acid is obtained from tert-butyl 2-(3-hydroxypropoxymethyl)-6-methylbenzoate and 5-cyclohexyl-2-p-tolyloxazol-4-ylmethyl iodide in analogy to example 1.

C29H35NO5 (477.25): LCMS (ESI): 478.52 [MH+].

Example 23

2-Methyl-6-[3-(5-phenyl-2-p-tolyloxazol-4-ylmethoxy)propoxymethyl]benzoic acid

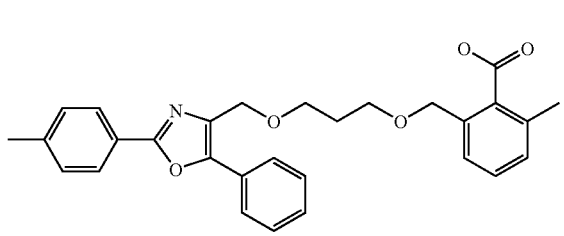

2-Methyl-6-[3-(5-phenyl-2-p-tolyloxazol-4-ylmethoxy)propoxymethyl]benzoic acid is obtained from tert-butyl 2-(3- hydroxypropoxymethyl)-6-methylbenzoate and 5-phenyl-2-p-tolyloxazol-4-ylmethyl iodide in analogy to example 1.
C29H29NO5 (471.20): LCMS (ESI): 472.52 [MH+].

Example 24

2-{3-[2-(4-Fluorophenyl)oxazol-4-ylmethoxy]-2,2-dimethylpropoxymethyl}-6-methyl-benzoic acid

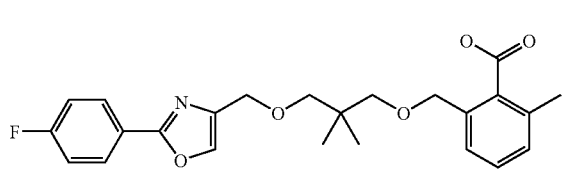

2-{3-[2-(4-Fluorophenyl)oxazol-4-ylmethoxy]-2,2-dimethylpropoxymethyl}-6-methyl-benzoic acid is obtained from tert-butyl 2-(3-hydroxy-2,2-dimethylpropoxymethyl)-6-methylbenzoate and 2-(4-fluorophenyl)oxazol-4-ylmethyl iodide in analogy to example 1.
C24H26FNO5 (427.18): LCMS (ESI): 428.24 [MH+].

Example 25

2-[2,2-Dimethyl-3-(5-methyl-2-p-tolyloxazol-4-ylmethoxy)propoxymethyl]-6-methyl-benzoic acid

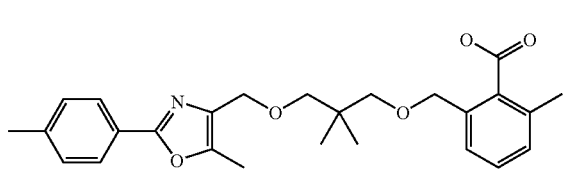

2-[2,2-Dimethyl-3-(5-methyl-2-p-tolyloxazol-4-ylmethoxy)propoxymethyl]-6-methyl-benzoic acid is obtained from tert-butyl 2-(3-hydroxy-2,2-dimethylpropoxymethyl)-6-methylbenzoate and 5-methyl-2-p-tolyloxazol-4-ylmethyl iodide in analogy to example 1.
C26H31NO5 (437.22): LCMS (ESI): 438.53 [MH+].

Example 26

2-{3-[2-(4-Fluorophenyl)-5-methyloxazol-4-ylmethoxy]-2,2-dimethylpropoxymethyl}-6-methyl-benzoic acid

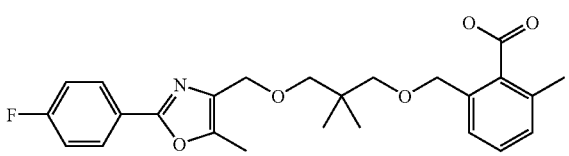

2-{3-[2-(4-Fluorophenyl)-5-methyloxazol-4-ylmethoxy]-2,2-dimethylpropoxymethyl}-6-methylbenzoic acid is obtained from tert-butyl 2-(3-hydroxy-2,2-dimethylpropoxymethyl)-6-methylbenzoate and 2-(4-fluorophenyl)-5-methyloxazol-4-ylmethyl iodide in analogy to example 1.
C25H28FNO5 (441.20): LCMS (ESI): 442.27 [MH+].

Example 27

2-{3-[2-(3-Methoxyphenyl)-5-methyloxazol-4-ylmethoxy]-2,2-dimethylpropoxymethyl}-6-methyl-benzoic acid

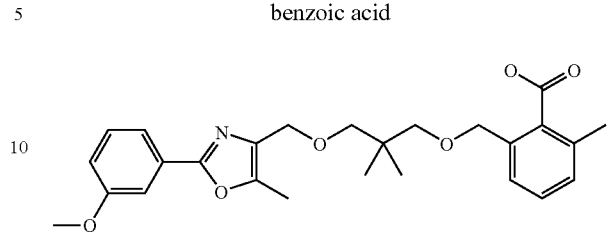

2-{3-[2-(3-Methoxyphenyl)-5-methyloxazol-4-ylmethoxy]-2,2-dimethylpropoxymethyl}-6-methylbenzoic acid is obtained from tert-butyl 2-(3-hydroxy-2,2-dimethylpropoxy-methyl)-6-methylbenzoate and 2-(3-methoxyphenyl)-5-methyloxazol-4-ylmethyl iodide in analogy to example 1.
C26H31NO6 (453.22): LCMS (ESI): 454.11 [MH+].

Example 28

2-{3-[5-Isopropyl-2-(3-trifluormethylphenyl)oxazol-4-ylmethoxy]-2,2-dimethylpropoxy-methyl}-6-methylbenzoic acid

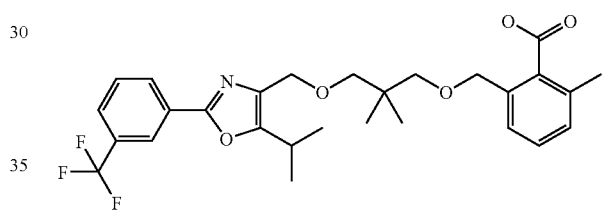

2-{3-[5-Isopropyl-2-(3-trifluoromethylphenyl)oxazol-4-ylmethoxy]-2,2-dimethyl-propoxymethyl}-6-methylbenzoic acid is obtained from tert-butyl 2-(3-hydroxy-2,2-dimethylpropoxymethyl)-6-methylbenzoate and 5-isopropyl-2-(3-trifluoromethyl-phenyl)oxazol-4-ylmethyl iodide in analogy to example 1.
C28H32F3NO5 (519.22): LCMS (ESI): 520.46 [MH+].

Example 29

2-Methyl-6-{4-[5-methyl-2-(4-fluorophenyl)oxazol-4-ylmethoxy]butoxymethyl}benzoic acid

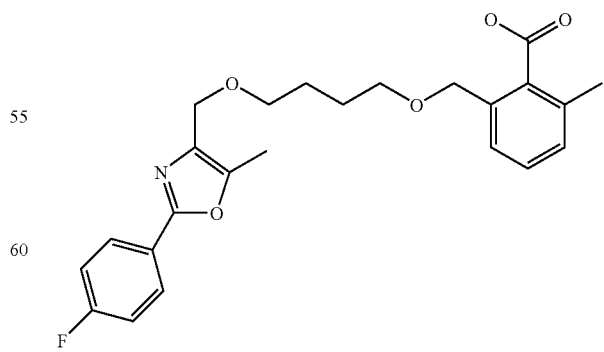

2-Methyl-6-{4-[5-methyl-2-(4-fluorophenyl)oxazol-4-ylmethoxy]butoxymethyl}benzoic acid is obtained from tert-butyl 2-(4-hydroxybutoxymethyl)-6-methylbenzoate and 5-methyl-2-(4-fluorophenyl)oxazol-4-ylmethyl iodide in analogy to example 1.

C24H26FNO5 (427.18): LCMS (ESI): 428.45 [MH+].

Example 30

2-Methyl-6-[4-(5-methyl-2-p-tolyloxazol-4-yl-methoxy)butoxymethyl]benzoic acid

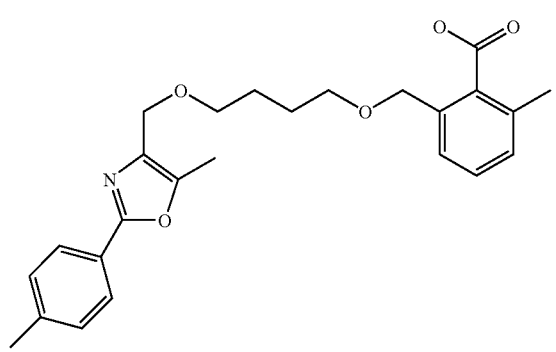

2-Methyl-6-[4-(5-methyl-2-p-tolyloxazol-4-ylmethoxy)butoxymethyl]benzoic acid is obtained from tert-butyl 2-(4-hydroxybutoxymethyl)-6-methylbenzoate and 5-methyl-2-p-tolyloxazol-4-ylmethyl iodide in analogy to example 1.

C25H29NO5 (423.20): LCMS (ESI): 424.27 [MH+].

Example 31

2-Methyl-6-{4-[2-(3-methoxyphenyl)-5-methyloxazol-4-ylmethoxy]butoxymethyl}-benzoic acid

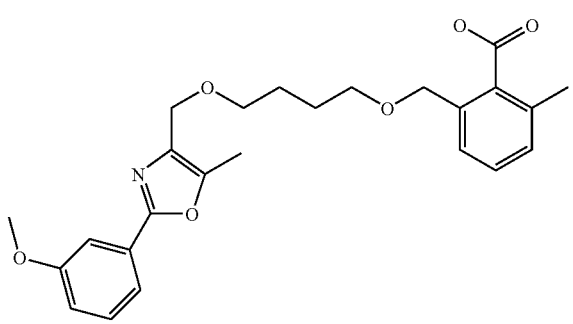

2-Methyl-6-{4-[2-(3-methoxyphenyl)-5-methyloxazol-4-ylmethoxy]butoxymethyl}-benzoic acid is obtained from tert-butyl 2-(4-hydroxybutoxymethyl)-6-methylbenzoate and 2-(3-methoxyphenyl)-5-methyloxazol-4-ylmethyl iodide in analogy to example 1.

C25H29NO6 (439.20): LCMS (ESI): 440.15 [MH+].

Example 32

2-{4-[5-Isopropyl-2-(3-trifluoromethylphenyl)oxazol-4-ylmethoxy]butoxymethyl}-6-methylbenzoic acid

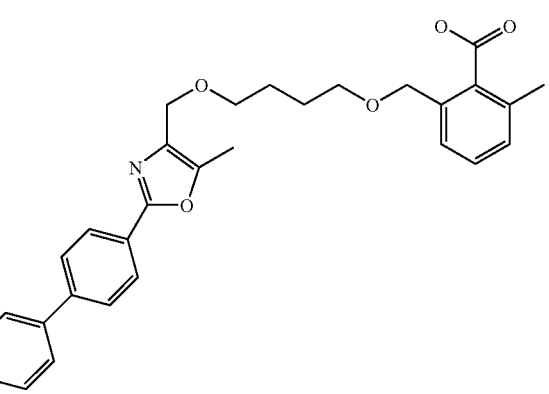

2-{4-[5-isopropyl-2-(3-trifluoromethylphenyl)oxazol-4-ylmethoxy]butoxymethyl}-6-methylbenzoic acid is obtained from tert-butyl 2-(4-hydroxybutoxymethyl)-6-methylbenzoate and 5-isopropyl-2-(3-trifluoromethylphenyl)oxazol-4-ylmethyl iodide in analogy to example 1.

C27H30F3NO5 (505.21): LCMS (ESI): 506.30 [MH+].

Example 33

2-Methyl-6-[4-(2-p-biphenyl-5-methyloxazol-4-yl-methoxy)butoxymethyl]benzoic acid 2-Methyl-6-[4-(2-p-biphenyl-5-methyloxazol-4-ylmethoxy)butoxymethyl]benzoic acid is obtained from tert-butyl 2-(4-hydroxybutoxymethyl)-6-methylbenzoate and 2-p-biphenyl-5-methyloxazol-4-ylmethyl iodide in analogy to example 1.

C30H31NO5 (485.22): LCMS (ESI): 486.47 [MH+].

What is claimed is:

1. A compound of formula I

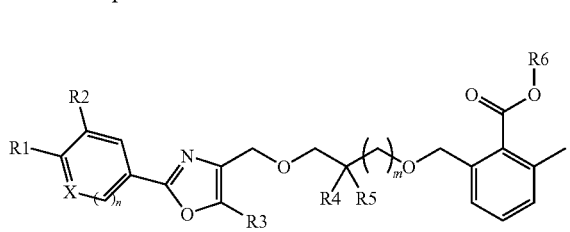

wherein:
R1 is selected from the group consisting of H, (C1-C6)-alkyl, O—(C1-C2)-alkyl, (C1-C6)-alkylmercapto, trifluoromethoxy, trifluoromethylmercapto, F, CF3, phenyl and phenoxy;
R2 is selected from the group consisting of H, O—(C1-C3)-alkyl, (C1-C3)-alkyl, $CF_3$ and trifluoromethoxy; or
R1 and R2 are fused together with the phenyl ring to form a naphthyl;
R3 is selected from the group consisting of (C1-C6)-alkyl, phenyl, and cyclohexyl;
R4 and R5 independently are H or $CH_3$, provided that when one of R4 and R5 is CH3, m then must be 1;
R6 is selected from the group consisting of H and (C1-C6)-alkyl;
X is CH, if n=1, or S if n=0;
n is 0 or 1; and
m is 1 or 2;
or a pharmaceutically acceptable salt thereof.

2. The compound according to claim 1, wherein one of R1 and R2 is not H; or a pharmaceutically acceptable salt thereof.

3. The compound according to claim 1, wherein:
R1 is H;
R2 is selected from the group consisting of O—(C1-C3)-alkyl, (C1-C3)-alkyl, $CF_3$ and trifluoromethoxy;
R3 is (C1-C6)-alkyl;
R4, R5 and R6 are H;
X is CH;
n is 1; and
m is 1;
or a pharmaceutically acceptable salt thereof.

4. The compound according to claim 1, wherein:
R1 is selected from the group consisting of (C1-C6)-alkyl, O—(C1-C2)-alkyl, trifluoromethoxy, trifluoromethylmercapto, F, phenyl and phenoxy;
R2 is H;
R4, R5 and R6 are H;
X is CH;
n is 1; and
m is 1;
or a pharmaceutically acceptable salt thereof.

5. The compound according to claim 1, wherein:
R1 and R2 independently are H, Me, O—$CH_3$, or
R1 and R2 are fused together with the phenyl ring to form naphthyl;
R3 is (C1-C6)-alkyl;
R4, R5 and R6 are H;
X is CH;
n is 1; and
m is 1;
or a pharmaceutically acceptable salt thereof.

6. The compound according to claim 1, wherein:
R1 is selected from the group consisting of H, F and $CH_3$;
R2 is selected from the group consisting of H, O—$CH_3$ and $CF_3$;
R3 is (C1-C6)-alkyl;
R4 and R5 are $CH_3$;
R6 is H;
X is CH;
n is 1; and
m is 1;
or a pharmaceutically acceptable salt thereof.

7. The compound according to claim 1,
wherein:
R1 is selected from the group consisting of H, F, $CH_3$ and phenyl
R2 is selected from the group consisting of H, O—CH, $CH_3$ and $CF_3$;
R3 is (C1-C6)-alkyl;
R4, R5 and R6 are H;
X is CH;
n is 1; and
m is 2;
or a pharmaceutically acceptable salt thereof.

8. A pharmaceutical composition comprising at least one compound according to claim 1 or a pharmaceutically acceptable salt thereof in combination with a pharmaceutically acceptable carrier.

9. The pharmaceutical composition according to claim 8, further comprising at least one-secondary pharmaceutically active compound wherein the secondary pharmaceutically active compound is effective in the therapeutic treatment of metabolic disturbance or a disorders associated therewith.

10. The pharmaceutical composition according to claim 9 wherein the secondary pharmaceutically active compound is an anti diabetic compound.

11. The pharmaceutical composition according to claim 9 wherein the secondary pharmaceutically active compound is a lipid modulator.

12. A method for treating a disorder of fatty acid metabolism or glucose utilization disorder, in a patient in need thereof, comprising administering to the patient a pharmaceutically effective amount of the compound according to claim 1 or a pharmaceutically acceptable salt thereof.

13. A method for treating a disorder in which insulin resistance is involved, in a patient in need thereof; comprising administering to the patient a pharmaceutically effective amount of the compound according to claim 1 or a pharmaceutically acceptable salt thereof.

14. A method for treating a disorders of diabetes mellitus or a physiological manifestation associated therewith, in a patient in need thereof; comprising administering to the patient a pharmaceutically effective amount of the compound according to claim 1 or a pharmaceutically acceptable salt thereof.

15. A method for treating dyslipidemia or a physiological manifestation associated therewith, in a patient in need thereof, comprising administering to the patient a pharmaceutically effective amount of the compound according to claim 1 or a pharmaceutically acceptable salt thereof.

16. A method for treating a condition associated with the metabolic syndrome or a physiological manifestation associated therewith, in a patient in need thereof, comprising administering to the patient a pharmaceutically effective amount of the compound according to claim 1 or a pharmaceutically acceptable salt thereof.

17. A method for treating a disorder of fatty acid metabolism or glucose utilization disorder or a physiological manifestation associated therewith, in a patient in need thereof, comprising administering to the patient a pharmaceutically effective amount of the compound according to claim 1 or a pharmaceutically acceptable salt thereof.

18. A method for treating a disorder in which insulin resistance is involved or a the physiological manifestation associated therewith, in a patient in need thereof, comprising administering to the patient a pharmaceutically effective amount of the compound according to claim 1 or a pharmaceutically acceptable salt thereof.

19. A process for producing a pharmaceutical composition comprising at least one compound according to claim 1 or a pharmaceutically acceptable salt thereof which comprises mixing the compound according to claim 1 or the pharmaceutically acceptable salt thereof with a pharmaceutically suitable carrier, and bringing this mixture into a form suitable for administration.

20. A compound, which is 2-{3-[2-(4-Fluorophenyl)oxazol-4-ylmethoxy]-2,2-dimethylpropoxymethyl}-6-methylbenzoic acid, or a pharmaceutically acceptable salt thereof.

21. A pharmaceutical composition comprising the compound according to claim 20 or a pharmaceutically acceptable salt thereof in combination with a pharmaceutically acceptable carrier.

* * * * *